(12) United States Patent
Knudsen (10) Patent No.: US 10,416,672 B2
(45) Date of Patent: Sep. 17, 2019

(54) METHOD AND AN UNMANNED AERIAL VEHICLE FOR DETERMINING EMISSIONS OF A VESSEL

(71) Applicant: Explicit I/S, Kgs. Lyngby (DK)

(72) Inventor: Jon Knudsen, Kgs. Lyngby (DK)

(73) Assignee: Explicit I/S, Lyngby (DK)

(*) Notice: Subject to any disclaimer, the term of this patent is extended or adjusted under 35 U.S.C. 154(b) by 331 days.

(21) Appl. No.: 15/114,869

(22) PCT Filed: Jan. 27, 2015

(86) PCT No.: PCT/EP2015/051584
§ 371 (c)(1),
(2) Date: Jul. 28, 2016

(87) PCT Pub. No.: WO2015/113962
PCT Pub. Date: Aug. 6, 2015

(65) Prior Publication Data
US 2017/0003684 A1    Jan. 5, 2017

(30) Foreign Application Priority Data

Jan. 28, 2014  (EP) .................................. 14152823
Oct. 3, 2014  (EP) .................................. 14187648

(51) Int. Cl.
*G01N 31/00* (2006.01)
*G05D 1/00* (2006.01)
(Continued)

(52) U.S. Cl.
CPC ......... *G05D 1/0094* (2013.01); *B64C 39/024* (2013.01); *G01M 15/102* (2013.01);
(Continued)

(58) Field of Classification Search
CPC .... G05D 1/0094; G05D 1/101; B64C 39/024; G01M 15/102; G01N 1/2273;
(Continued)

(56) References Cited

U.S. PATENT DOCUMENTS 5,742,053 A    4/1998  Rekunyk
8,232,104 B1*  7/2012  Frazier .................. C06B 23/008
                                                    436/164
(Continued)

FOREIGN PATENT DOCUMENTS

CA    2651460    11/2007
CN    101876717  11/2010
(Continued)

OTHER PUBLICATIONS

McGonigle, A. et al, "Unmanned aerial vehicle measurements of volcanic carbon dioxide fluxes", Geophysical Research Letters, vol. 35, L06303, (2008).

*Primary Examiner* — Toan M Le
*Assistant Examiner* — Xiuqin Sun
(74) *Attorney, Agent, or Firm* — McHale & Slavin, P.A.

(57) ABSTRACT

A method for determining emissions in an exhaust plume (11) produced by a combustion engine of a vessel (10) during cruise of the vessel (10), said emissions including the presence or concentration of carbon dioxide ($CO_2$) and/or sulphur dioxide ($SO_2$) and/or the count and size of particles. The position and distribution of the exhaust plume (11) is determined or estimated on the basis of the position, bearing and speed of the vessel (10) and further on the basis of meteorological data, such as wind direction and speed. An unmanned aerial vehicle (UAV) (12), i.e. a so-called drone, is controlled to fly through the 10 plume (11) to make measurements of exhaust emissions of the vessel (10).

16 Claims, 6 Drawing Sheets

(51) Int. Cl.
*G01M 15/10* (2006.01)
*G01N 21/51* (2006.01)
*G01N 1/22* (2006.01)
*G07C 5/00* (2006.01)
*B64C 39/02* (2006.01)
*G01N 21/3504* (2014.01)
*G01N 27/416* (2006.01)
*G01N 33/00* (2006.01)
*G01W 1/02* (2006.01)
*G05D 1/10* (2006.01)
*G01N 1/02* (2006.01)

(52) U.S. Cl.
CPC ....... *G01N 1/2273* (2013.01); *G01N 21/3504* (2013.01); *G01N 21/51* (2013.01); *G01N 27/4162* (2013.01); *G01N 33/004* (2013.01); *G01N 33/0042* (2013.01); *G01W 1/02* (2013.01); *G05D 1/101* (2013.01); *G07C 5/008* (2013.01); *G01N 2001/021* (2013.01); *G01N 2001/2279* (2013.01)

(58) Field of Classification Search
CPC ............... G01N 21/3504; G01N 21/51; G01N 27/4162; G01N 33/004; G01N 33/0042; G01N 2001/021; G01N 2001/2279; G01W 1/02; G07C 5/008

USPC .......................................................... 702/24
See application file for complete search history.

(56) References Cited

U.S. PATENT DOCUMENTS

| | | | |
|---|---|---|---|
| 8,527,179 B2* | 9/2013 | Tabares | F02D 41/0235 701/101 |
| 2004/0189976 A1 | 9/2004 | Burns et al. | |
| 2010/0206042 A1 | 8/2010 | Johns et al. | |
| 2011/0251800 A1* | 10/2011 | Wilkins | G01J 3/02 702/24 |
| 2012/0092649 A1* | 4/2012 | Wong | G01W 1/00 356/72 |
| 2013/0289899 A1 | 10/2013 | Tolton et al. | |

FOREIGN PATENT DOCUMENTS

| | | |
|---|---|---|
| CN | 201707324 | 1/2011 |
| CN | 102301230 | 12/2011 |
| WO | WO2009156437 | 12/2009 |
| WO | WO2012046180 | 4/2012 |

\* cited by examiner

METHOD AND AN UNMANNED AERIAL VEHICLE FOR DETERMINING EMISSIONS OF A VESSEL

CROSS REFERENCE TO RELATED APPLICATIONS

This is a national stage filing in accordance with 35 U.S.C. § 371 of PCT/EP2015/051584, filed Jan. 27, 2015, which claims the benefit of the priority of European Patent Application No. 14152823.2, filed Jan. 28, 2014 and European Patent Application No. 14187648.2, filed Oct. 3, 2014 the contents of each are incorporated herein by reference.

TECHNICAL FIELD

The present invention relates to a method for determining emissions in an exhaust plume produced by a combustion engine of a vessel, in particular for determining the presence or concentration of at least one predetermined gas or the count and size of particles in the exhaust plume. The invention also related to an unmanned aerial vehicle for determining such emissions.

BACKGROUND OF THE INVENTION

Transportation of goods at sea constitutes a significant source of air pollution and greatly influences the quality of air in many cities around the globe. According to research reports, health costs related to the treatment of diseases caused by ship traffic amount to some estimated €60 billion annually in Europe alone, corresponding to approximately 10% of all health costs associated with the effects of air pollution in the region. In Europe, emissions from vessels cause an estimated 50,000 premature deaths per year.

In order to reduce the environmental impact of ship traffic, the European Union and the International Maritime Organization have implemented regulations aimed at reducing emissions, in particular a reduction of the emissions of $SO_2$ and $NO_2$. Certain control areas, so-called Sulphur Emission Control Areas (SECAs), have been defined globally in which enhanced emission restrictions apply. When entering such areas, vessels are required to use low-emission fuel, whereas other and cheaper types of fuel may be used outside SECAs. Accordingly, most modern vessels are equipped with two fuel tanks, of which one holds SECA-compliant fuel and another one is for non-SECA-compliant fuel. Commonplace fuels include heavy fuel oil (HFO) having a sulphur concentration of about 2.5% and marine diesel oil (MDO) with a sulphur concentration of about 1% (after Jan. 1, 2015: 0.1%).

The adaptation of environmental regulations also increases the demand for national authorities' control of vessel emissions. However, no reliable and cost-efficient procedure for performing exhaust measurements of plumes of vessels has been developed so far. Accordingly, it has not been possible hitherto to efficiently control emissions of vessels, and it may be suspected that many vessels do not carry out the required shift to SECA-compliant fuel when entering SECAs. A need hence exists for new technologies which enable national and international maritime organizations to enforce environmental regulations.

SUMMARY OF THE INVENTION

On the above background it is an object of the invention to provide a cost-efficient and reliable method for monitoring emissions of vessels with a view to enabling enforcement of applicable emission regulations.

In a first aspect, the invention thus provides a method for determining emissions in an exhaust plume produced by a combustion engine of a vessel during cruise of the vessel, said emissions comprising the presence or concentration of at least one predetermined gas or the count and size of particles, the method comprising the steps of:
  identifying the vessel, its position, bearing and speed;
  determining meteorological conditions in an area cruised by the vessel;
  providing an unmanned aerial vehicle (UAV) comprising:
    an electronic control system for controlling the vehicle's flight;
    at least one sensor for determining emissions in the atmosphere surrounding the vehicle;
    a data interface of passing signals to an external data collecting unit, said signals comprising at least one of: (a) an output signal of the at least one sensor and (b) data obtained from the output signal of the at least one sensor;
  determining a position and distribution of the exhaust plume on the basis of the position, bearing and speed of the vessel and further on the basis of said meteorological conditions;
  controlling the UAV to:
    fly through the exhaust plume;
    determine said emissions in the exhaust plume by means of the at least one sensor; and
    transmit said signals to an external data collecting unit for further processing thereof.

Thanks to the provision of the UAV, it is possible to determine emissions during cruise of the vessel by accessing the exhaust plume of the vessel during operation of the UAV. Accordingly, it may, for example, be immediately detected if a ship cruising in a SECA region adequately runs on SECA-compliant fuel. The determination of emissions is non-invasive in the sense that it does not require the presence of equipment or personnel on-board the vessel. Moreover, emissions can be determined without prior notice, and no doubt can subsequently be raised with regard to the source of the emissions detected by the UAV, inasmuch as position data, such as GPS data, of the UAV can be correlated with and recorded together with position data of the vessel, such as AIS (see below) and/or radar recordings. In most instances, the vessel can be identified on the basis of radar systems or radio communication with a commander or automatic position broadcasting system of the vessel, or even on the basis of camera recordings made by adequate camera equipment installed on the UAV.

In one preferred embodiment of the present invention, the at least one sensor comprises a so-called in situ sensor, which may be a non-optical sensor for chemically or electrochemically analysing gas and/or air coming into contact with a surface of the sensor. It has been found that the provision of a non-optical sensor, such as an electrochemical or NDIR sensor, may be advantageous over optical sensors, in particular remote optical sensors, in that NOx emissions may be precisely determined and in that particles, notably sulphur particles of concern in relation to vessel emissions, can be captured and assessed more precisely with a non-optical sensor than with an optical sensor.

As compared to the concept of so-called remote sensing, in situ sensing confers the advantage that the measured data can be associated with the exact environment of concern. In many instances, for measurements deriving from optical sensors to be applicable, certain assumptions have to be made with regard to, among other things, the engine of the vessel, such as for instance its rate of NOx emission at the applicable state of operation. Such assumptions are usually based, at least in part, on look-up tables and may lack accuracy, notably if reality differs from the assumptions. Such deviations may occur, for example, if the vessel reduces its NOx emissions, and may lead to erroneous results. In situ measurements overcome these disadvantages. Moreover, in situ sensing eliminates or reduces the risk of vessel identification errors, as the sensed data may be associated with a GPS position of the UAV and a time stamp.

As used herein the term "bearing" may in particular mean the course of the vessel.

The electronic control system for controlling the vehicle's flight may be operator-assisted, i.e. manually operated or programmed, or it may be configured for autonomously controlling the vehicle's flight, e.g. on the basis of sensor input.

The at least one sensor may be comprised in a sensor chamber, which may preferably be sealed, and which may comprise an air intake, e.g. a tube, and/or filter. The provision of a sensor chamber allows the at least one sensor, which preferably is constituted by one or more non-optical sensors, such as electrochemical sensors, confers the advantage that steady state measurements may be achieved. In particular, as the UAV moves during operation, the chamber avoids aerodynamic disturbances, such as turbulence. Moreover, the intake of air or gas into the chamber may be controlled, e.g. by a suction pump, such that a portion of air (or gas) of the plume entering the chamber can be associated with a distinct position within the plume. As mentioned, a suction pump may be provided for sucking air and/or gas into the chamber. A relay for optimising the readings of the at least one sensor may further be provided within the chamber or in the vicinity thereof.

In general, measurements in plumes from vessels are carried in environments with highly fluctuating gas concentrations. Sensors capable of reacting suitably fast have been found to be rather heavy and bulky and accordingly non-preferred by UAV applications. Accordingly, preferred embodiments of the present invention rely on comparatively light sensors which can be carried by a UAV without any difficulty. However, such light-weight sensors require steady state environments for them to perform sufficiently accurate measurements. In one embodiment, the sensor measurements are recorded at a certain, preferably optimal, position within the plume identified during flight. In one particularly advantageous embodiment, the at least one sensor is arranged in a closed chamber, the size of which provides a homogenous mass of air surrounding the sensor(s). The intake of air or gas into the chamber is preferably controlled, e.g. by a suction pump and a relay, which shuts the intake of air and/or gas when the desired position within the plume has been reached, such as when the concentration of certain gasses and/or particles exceed a predetermined threshold.

Accordingly, preferred embodiments of the invention for performing, by means of a UAV, measurements, notably of sulphur emissions, in plumes produced by moving vessels at sea include:

controlling the flight trajectory of the UAV during flight thereof, notably on the basis of vessel speed and course and/or meteorological conditions and/or sensor data, in situ sensor measurements by providing the at least one sensor in a chamber; and controlling intake of gas and/or air into the sensor chamber for achieving a homogenous steady state within the chamber, at the intended measurement site.

As used herein, the term "position and distribution" of the exhaust plume should be understood to include the determination of at least a position of the exhaust plume and a center line thereof. The method of the present invention may include the step of determining an optimal sampling point before and/or during flight on the basis of the position of the vessel, preferably its real-time position as acquired, e.g., through AIS data. In particular, the position and center line of the exhaust plume may be determined on the basis of the measured sensor data.

The step of controlling the UAV to fly through the exhaust plume may be performed on the basis of an autonomous flight control, notably on the basis of sampled sensor data.

At the step of flying the vehicle through the exhaust plume, the flight path may be continuously adjusted, preferably in real-time mode, in order to position the vehicle optimally within the plume.

During flight and data sample, the sample of emissions within the plume may be optimised by way of controlling the suction of air and/or gas into the sensor chamber once a predetermined concentration threshold is reached.

It should be understood that determination, including real-time determination of vessel position, course and speed, meteorological conditions, and/or detected changes in gas or particle concentrations may include determinations of rates of change of the said parameters.

The step of identifying the vessel, its position, bearing (i.e. course) and speed may be carried out by ordinary means, such as by The Automatic Identification System (AIS), by radar detection and/or by radio communication. As mentioned above, one or more appropriately configured cameras may be mounted to or integrated with the UAV as an alternative or supplemental means for determining the identity of the vessel.

The concentration of gas, which may be determined, may in particular include a concentration of carbon dioxide ($CO_2$) and/or a concentration of sulphur dioxide ($SO_2$). In particular, combined signals of $CO_2$ and $SO_2$ measurements, notably the $SO_2/CO_2$ ratio, may be utilized for determining the sulphur concentration of the fuel applied by the vessel. It is preferred that the measurements are carried out within areas of the plume, in which the presence of $CO_2$ emitted from the vessel engine's exhaust is predominant in relation to $CO_2$ deriving from other source. Sensors known per se may be deployed in the present invention. For the detection of $CO_2$ concentrations, a non-dispersive infrared (NDIR) sensor may preferably be applied, e.g. of the type which provides measurements in the range of 0-5000 ppm. A NDIR sensor is a spectroscopic device commonly used as a gas detector. Typically, the wavelength which passes through a sampling of the device is not pre-filtered. For the determination of concentrations of $SO_2$, an electrochemical sensor may preferably be deployed. Commonly available electrochemical gas sensors include gas detectors which determine the concentration of a target gas by oxidizing or reducing the target gas at an electrode and measuring the resulting current at the electrode. It has been found that the concentration of $SO_2$ as measured by an electrochemical sensor may require correction for the presence of $NO_2$. Accordingly, a further electrochemical sensor for detecting the presence of $NO_2$ may be applied.

The step of determining the position and distribution of the exhaust plume, including the optimal position for emissions sampling, preferably includes estimating, i.e. forecasting, pre-flight an expected or predictable position of the centre line of the plume at the point in time, at which the UAV is expected to fly through the plume. It preferably also includes the real time adjustment of the flight trajectory and speed during a UAV mission by way of updated data on the position of the vessel, meteorological conditions, including in particular wind data, and output signals from the at least one sensor, in order to optimise the UAV position along the centre line of the plume while sampling.

In order to enhance the accuracy of emission measurements, the invention may benefit from an adapted air intake tube and filter, in order to minimise wind gusts affecting the measurements, and a sealed sensor chamber hosting the at least one sensor. A pump may be provided to control or promote the flow of air into the chamber in order to obtain a steady state condition for the sensors.

In particular with regard to $CO_2$, embodiments of the invention may also comprise the step of taking the $CO_2$ concentration of the atmosphere outside of the exhaust plume into account. $CO_2$ not emitted from the vessel's engine may (at least around 400-440 ppm offset) occur naturally within the atmosphere or may derive from other sources. The non-vessel related $CO_2$ concentration may be measured by one or more sensors of the UAV, or it may be provided from an external source.

The at least one sensor may in one embodiment of the invention be configured to determined NOx concentrations.

The count or size of particles, notably soot particles, may be determined on the basis of one or more suitable sensors known per se mounted on or integrated with the UAV. In the immediate vicinity of the vessel, i.e. at distances of less than approximately 100 m, ultrafine particles with an average diameter of about 100 nm or less is of primary concern, whereas such particles may tend to grow to larger sizes at distances from the vessel of more than 100 m. The presence and count of particles may be determined by a particle counter known per se, e.g. of the type which detects and counts particles one at a time. Particle counting may, for example, be based upon light scattering, light obscuration, or direct imaging. A light source, such as a laser or halogen light source, is used to illuminate the particle as it passes through the detection chamber. The particle passes through the light source and if light scattering is used, the redirected light may be detected by a photo detector, the output of which may be used to determine the particle count.

In order to reduce the possible interference from radio frequency emitting components on-board the UAV on the signal of the at least one sensor, the invention may comprise the positioning of the sensor control board inside the sensor chamber.

The respective sensor outputs for gas concentrations and particle count measurements may be collected by the electronic control system of the UAV and adequately processed therein, or they may be transmitted to a remote on-shore or off-shore installation for further processing and evaluation.

In addition to emission data, the step of sampling sets of data of the present invention may preferably include the step of including, in each set of data, sensor data obtained by the at least one sensor, a time of the sample, and a position of the UAV at the time of the sample, so as to enable the sensor data to be correlated with a specific vessel, time and position. Preferably, the vehicle is navigated, autonomously or in an operated-assisted (i.e. remote-controlled) manner, to an optimal sampling point in the exhaust plume before the sets of data are collected or sampled.

Current or forecasted meteorological conditions in the area cruised by the vessel may be determined by ordinary means and may conveniently be obtained from meteorological services. The direction and speed of wind in the area cruised by the vessel is of interest with regard to being able to determine the position and distribution of the exhaust plume relative to the vessel. Other meteorological factors, such as humidity, temperature and/or the occurrence of rain may be taken into account in order to adequately compensate the emission measurements, or with a view to being able to assess the quality, i.e. precision of the obtained measurements. Whereas humidity and temperature have been found to have little influence on the quality of the obtainable measurements, the presence of rain may render detection of particles inaccurate. It is hence preferred that the concentration of particles be detected in non-rain conditions.

The UAV of the present invention may include a UAV (or "drone") known per se, i.e. an aircraft without a human pilot on board. Its flight may be controlled either autonomously by computers in the UAV itself, or under the remote control of a human pilot, or by a computerized control system on the ground or in another vehicle, vessel or the like. The typical launch and recovery method of an unmanned aircraft is by the function of an automatic system or an external operator on the ground. The UAV may be of the type having fixed wings and one or more thrust generating devices permanently attached to the vertical stabilizer or wings, or it may be of the multi-rotor type.

In one embodiment of the invention, a flight mission comprising at least a flight trajectory of the UAV may be determined prior to take off. For example, the flight trajectory may be governed by the position, speed and bearing (i.e. course) of the vessel or vessels which is/are the subject of the mission. The trajectory may further be determined on the basis of the designated measurement task. For example, in respect of one vessel, the determination of a particle count may be desired at a first predetermined distance from the vessel, whereas in respect of another vessel, the determination of a particle count may have to be obtained at a second predetermined distance from the vessel.

Alternatively to determining the flight mission prior to take off of the UAV, or in addition thereto, the flight mission may be determined, redefined or adjusted during flight based, e.g., on changes in the conditions controlling the flight trajectory. For example, the control system of the UAV may be programmed to automatically adjust the UAV's exact flight trajectory and speed through the exhaust plume of the vessel in order to navigate the UAV towards a specific region of interest within the exhaust plume, such as a region of the highest determinable gas concentration or particle count (the optimal sampling point). Accordingly, adjustment of the flight trajectory during flight may, in one embodiment, be based upon the input of the gas and particle sensors, meteorological conditions, notably wind data, and data relating to vessel position, speed and course, and time derivatives of the aforementioned data. In particular, the flight trajectory may thus be adjusted on the basis of at least output signals of the at least one sensor, whereby adjusting the flight trajectory may comprise repeatedly determining a rate of change of a concentration, including particle count, of the emissions. In order to navigate the UAV towards regions of high concentration, the flight trajectory may be adjusted in case the rate of change of concentration is negative.

The flight trajectory may also be adjusted during flight if a change of meteorological conditions necessitate a change of trajectory, and/or if a vessel of interest for the mission changes its speed or course, and/or if vessels other than those originally designated for the mission are to be included in the mission. The trajectory may also be adjusted during flight in response to fuel consumption of the vessel, remaining battery capacity of the UAV, or any other parameter detectable by on-board equipment or by remote equipment, or on the basis of human intervention from a remote control facility.

The trajectory of the UAV is in particular governed by its heading and/or an altitude, but may include other parameters, such as its speed.

In one embodiment of the invention, the flight trajectory may be controlled to fly the UAV, at least during part of its flight within the plume, at a speed and direction which is approximately equal to the vector sum of the speed and direction of the vessel and a current average speed and direction of wind at the vessel's position. It may hence be possible to fly the UAV within a particular mist of particles and emission of gasses for a period of time, which allows taking into account a possible response time of the sensors of the UAV.

Alternatively, the UAV may be flown at an approximately constant distance from the vessel for a period of time in order to obtain or enhance a steady state condition for the sensors.

In one embodiment of the invention, the air suction into the sealed chamber hosting the at least one sensor may be paused by way of a relay controlling the on/off setting of the air suction pump once a predetermined gas concentration and/or particle count threshold is reached. It may hence be possible to optimise sampling by way of allowing the air flow inside the chamber to stabilise in order to obtain a steady state condition for the sensors.

As used herein, the speed, altitude and direction of the UAV should be understood as speed, altitude and direction relative to ground, as determinable by means of, e.g., GPS. Likewise the speed and direction of wind, and the speed and direction of the vessel should be understood as speed and direction relative to ground.

The step of processing signals obtained by the sensor measurements may comprise the step of comparing the emissions as determined by the at least one sensor to predetermined threshold emission values. Data may be collected in a memory on board the UAV and/or transmitted to a remote control and/or data collection facility. The predetermined threshold emission values may typically be determined on the basis of official regulations as regards emissions, such as those applicable in SECAs.

In a second independent aspect, the invention also provides an unmanned aerial vehicle (UAV) suitable for use in the method according to the first aspect of the invention, i.e. a UAV for determining emissions comprising the presence or concentration of at least one predetermined gas or the count and size of particles, the UAV comprising:

an electronic control system for controlling the vehicle's flight;
at least one sensor for determining emissions in the atmosphere surrounding the vehicle;
a data interface of passing signals to an external data collecting unit, said signals comprising at least one of: (a) an output signal of the at least one sensor and (b) data obtained from the output signal of the at least one sensor;

the UAV being controllable to:
fly through an area of interest;
determine said emissions in the area of interest by means of the at least one sensor;
transmit said signals to an external data collecting unit for further processing thereof.

The at least one sensor may be provided at an outer surface of a part of the UAV, or it may be provided within a housing structure of the UAV. In the latter alternative, a plurality of sensors may be arranged in series along a single flow conduit within the housing structure. A pump may be provided to control or promote the flow of air into and through the conduit.

The description of the UAV set forth herein in connection with the disclosure of the method according to the first aspect of the invention also apply to the UAV according to the second aspect of the invention.

BRIEF DESCRIPTION OF THE DRAWINGS

Embodiments of the invention will now be further described with reference to the drawings, in which.

DETAILED DESCRIPTION OF THE DRAWINGS

Figure 1A:
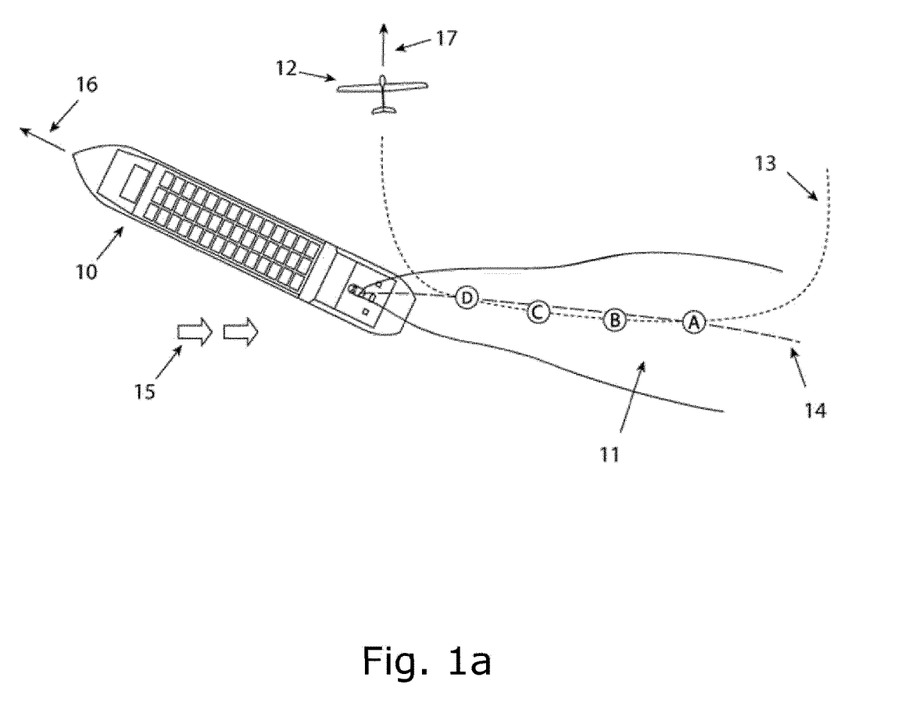
FIG. 1a shows a vessel, its exhaust plume and the flight trajectory of a UAV in one embodiment of the invention seen from above.

FIG. 1a shows a top view of a vessel 10, its exhaust plume 11 and the flight trajectory 13 of a UAV 12 in one embodiment of the invention. In one embodiment (not shown), the UAV may zig-zag through the exhaust plume. As shown, the UAV 12 navigates from behind the exhaust plume 11 along the centre line of the plume 14 towards the vessel 10. At position A, the exhaust plume entry point, the gas and particle sensors of the UAV 12 determine an increased concentration of emissions, and the UAV 12 starts its flight path along the centre line of the plume 14 towards position D, the optimal sampling point. At positions B through C (or multiples hereof), the UAV 12 is adjusted—or adjusts itself—to remain on course along the centre line of the plume 14 towards the vessel. Adjustments are made based on real-time changes in vessel 10 position, course and speed, meteorological conditions 15, and/or detected changes in gas or particle concentrations. Sampling is done continuously throughout the mission. Once reaching position D, the air speed of the UAV 12 is adjusted—or adjusts itself—along with adjustments in GPS position in order to maintain constant distance to the vessel 10 at the centre line of the exhaust plume 14 for optimal sampling.

Figure 1B:
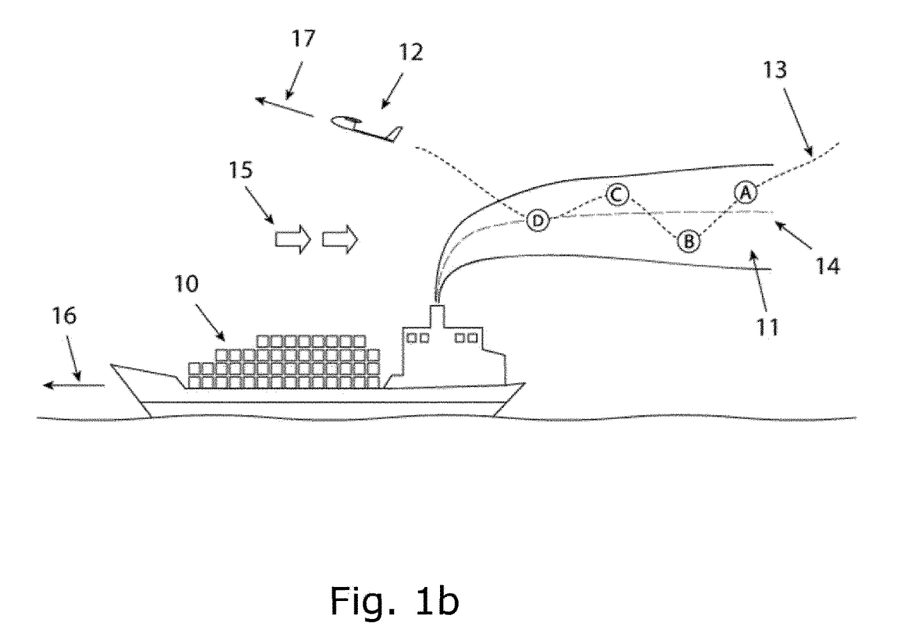
FIG. 1b illustrates the vessel, exhaust plume and flight trajectory of the embodiment of FIG. 1 in a side view.
Figure 2:
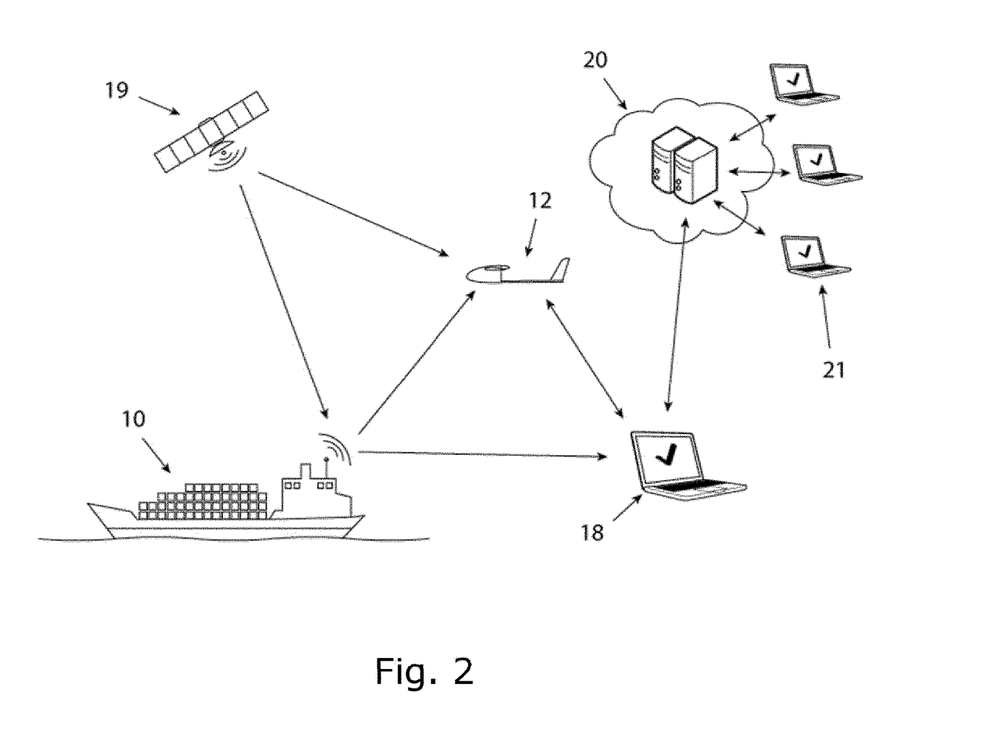
FIG. 2 generally depicts hardware components applicable in a preferred embodiment of the invention.
Figure 3:
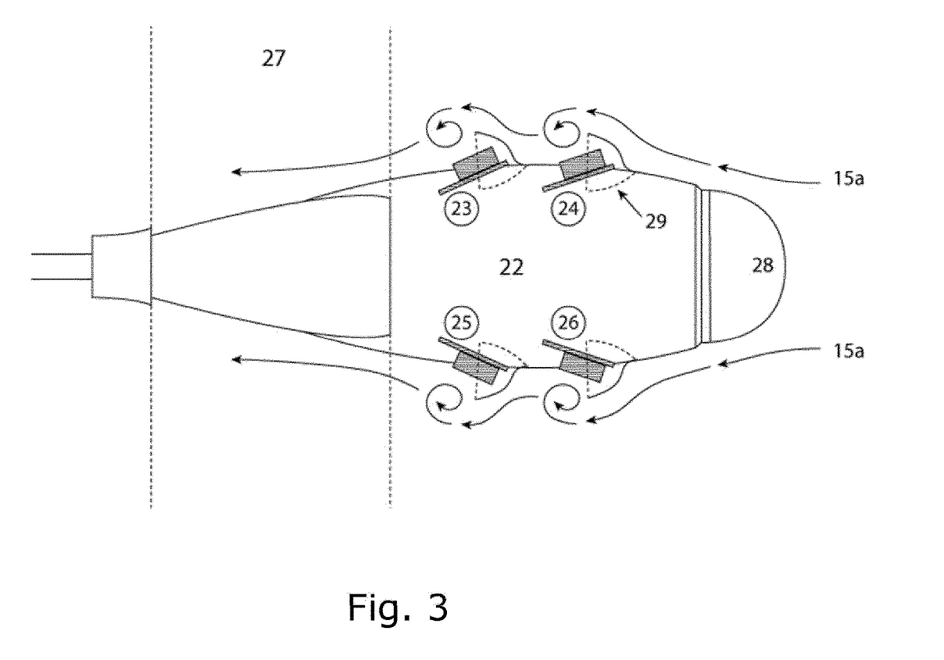
FIG. 3 illustrates a first embodiment of a sensor configuration of a UAV for determining emissions.
Figure 4:
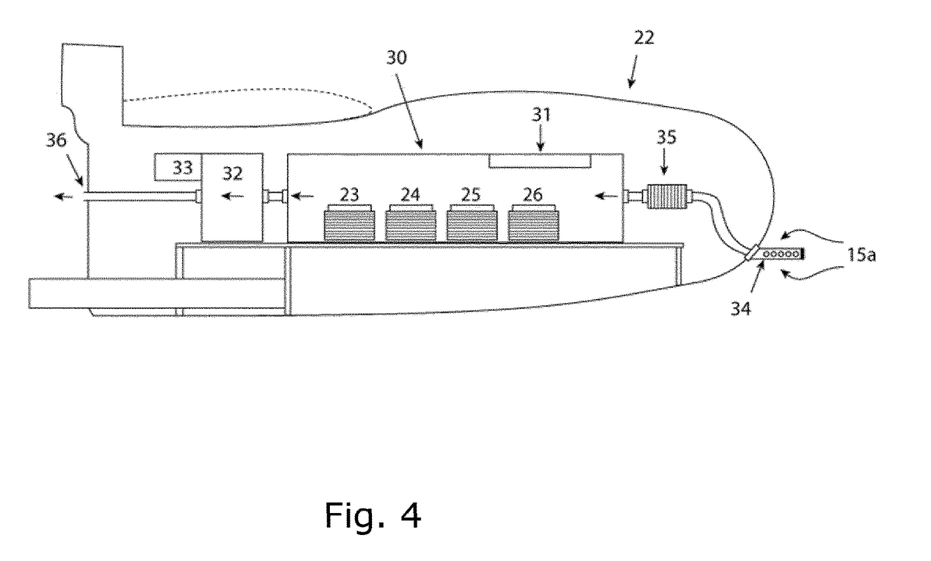
FIG. 4 illustrates a second embodiment of a sensor configuration of a UAV for determining emissions.
Figure 5:
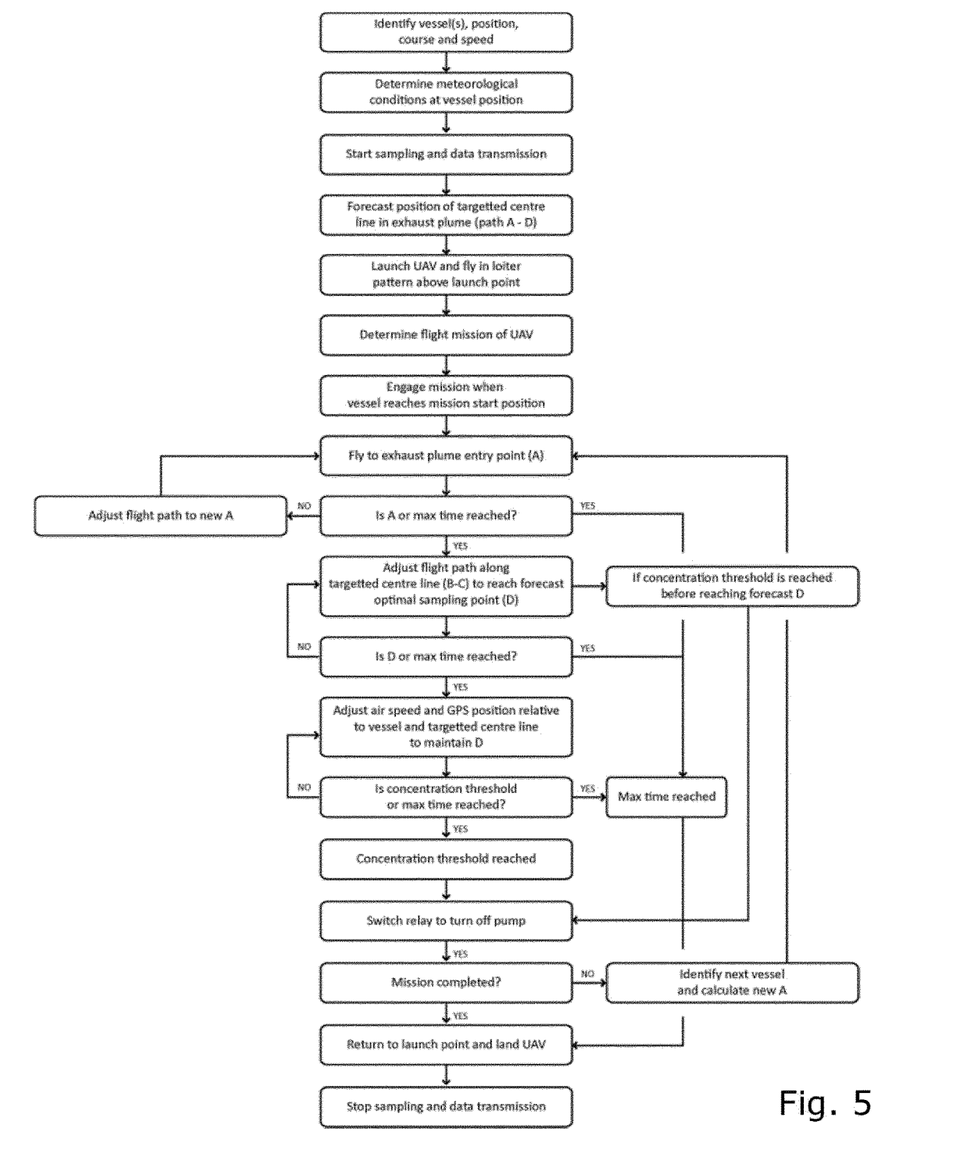
FIG. 5 is a flow chart generally illustrating the steps of one embodiment of the method according to the first aspect of the invention.

After reaching D, defined at the optimal sampling point, and remaining there until concentration levels reach a predetermined threshold, the UAV 12 exists the plume 11. The flight trajectory 13 is shown in a side view in FIG. 1b. As shown, the UAV 12 may fly at variable latitudes, longitudes and altitudes as well as speeds through the plume 11 in order to optime the flight path for sampling. In FIGS. 1a and 1b, the direction of wind is indicated by arrows 15, the bearing of the vessel 10 is indicated by arrows 16, and the heading of the UAV 12 is indicated by arrows 17. The UAV 12 may alternatively be controlled to fly through the plume 11 at a fixed altitude and/or along a pre-programmed flight trajectory.

At position D, the flight trajectory 13 may be adjusted to fly the UAV 12 at a speed and direction which is approximately equal to the vector sum of the speed and direction of the vessel 10 and a current average speed and direction of wind at the vessel's 10 position. The UAV 12 may hence be flown within a particular mist of particles and emission of gasses for a period of time, which allows taking into account a possible response time of the sensors of the UAV and/or adjustments in the conditions governing the optimal flight trajectory. Alternatively, at position D the UAV may be flown at an approximately constant distance from the vessel 10 for a certain period of time in order to obtain a steady state condition for the sensors.

FIG. 2 generally depicts hardware components applicable in a preferred embodiment of the invention. The vessel 10 may communicate signals, such as position and course signals, to a remote control facility 18, e.g. via the AIS. The remote control facility 18 in turn controls the UAV 12 based on received sensor, position and other signals transmitted from the UAV 12 or other sources. Position and course signals of the vessel 10 may also be captured by the UAV 12 and subsequently relayed to the remote control facility 18. Satellite 19 is provided for GPS control and position determination of the UAV 12 and vessel 10. Sample diagnostics may be performed both on-board the UAV during flight or by the remote control facility 18. Once analysed, the remote control facility 18 uploads all data including vessel information, mission log, sample data and diagnostics results to a cloud-based storage facility 20 accessible by various remote user devices 21.

FIG. 3 illustrates a first embodiment of a sensor configuration of a UAV for determining emissions, wherein sensors, including gas sensors and/or particle counters 23, 24, 25, and 26 are mounted externally on a structure 22, which in turn attaches to a wing 27 of the UAV 12, the structure having a rounded front tip 28. As the UAV moves relative to incoming wind 15*a*, air vortices occur downstream of respective protective casings 29 of the sensors 23, 24, 25 and 26. In the vortices, the sensors 23, 24, 25 and 26 perform measurements, and output signals thereof are communicated through wired or wireless communication paths to a control system (not shown) of the UAV and/or directly to a remote control facility, such as control facility 30 shown in FIG. 2.

FIG. 4 illustrates a second embodiment of a sensor configuration inside a UAV fuselage 22 for determining emissions, wherein sensors, including gas sensors and/or particle counters 23, 24, 25, 26 are housed within a sealed sensor chamber 27 along with the sensor control board 28. The air 29 is sucked into the sensor chamber 27 using a pump 30 fitted with an on/off relay 31. In order to minimise effects of gusts in wind 15 (not shown), the air is guided via a perforated air intake tube 32, closed off at the tip, through a filter 33, into the sensor chamber 27. Air exits the sensor chamber 27 at outlet 34.

In FIGS. 3 and 4, each of the respective sensors 23, 24, 25 and 26 may serve its own purpose, i.e. be specifically designed for measuring a particular gas and/or count of particles.

For example, one of the four sensors in each embodiment may be for the measurement of $CO_2$, another one for the measurement of $SO_2$, a third one for measurement of $NO_2$, and a fourth one for the count of particles.

FIG. 5 is a flow chart generally illustrating the steps of one embodiment of the method according to the first aspect of the invention. Initially one or more vessels are identified along with its/their position, course and speed. Current or forecasted meteorological conditions at the position of the vessel(s) are then determined. On the basis of the vessel position, course, speed and meteorological conditions, the position of the targeted centre line of the vessel's exhaust plume is subsequently estimated/forecasted. The entire flight mission or a part of the flight mission for the UAV may then be determined prior to take off of the UAV.

Once launched the UAV will take up a loiter pattern above the launch point until such time when the vessel reaches the mission start position. This position is predetermined to ensure enough mission track along the centre line of the plume to perform a successful sampling.

Sampling is done continuously throughout the flight mission and sampled data are stored on-board as well as relayed real-time to the remote control facility. As the UAV arrives at the entry point of the plume (A), it is controlled to fly through the exhaust plume along the targeted centre line of the plume towards the optimal sampling point (D) at the determined speed. Once reaching D, the UAV will adjust its speed and position to remain at point D until such time when the predetermined concentration threshold is reached. The threshold triggers the on-board relay to stop the pump allowing the air inside the sensor chamber to settle long enough to mitigate the reaction time of the sensors and obtain steady state. In case the flight mission needs to be adjusted, the steps of entering (A) and navigating through (B-C) the plume towards the optimal sampling position (D), and remaining there are repeated taking into account real-time updated information of the vessel's position, course and speed, meteorological conditions, and/or sampled data.

Once the flight mission is completed, the UAV is returned for landing, unless the mission includes a further vessel of interest. In the latter case, the aforementioned steps of flying the UAV along the centre line of exhaust plume, determining emissions and other governing variables, transmitting sampled data and determining if the flight mission is to be adjusted are then repeated in respect of such next vessel.

If at any point in time during the mission, the max flight time according to the battery is reached while still ensuring the safe return of the UAV, the mission is aborted and the UAV is returned for landing.

If at any point in time from the entry into the plume (A) but prior to reaching (D) the concentration threshold is reached, the mission is deemed completed and the UAV is returned for landing, unless the mission includes a further vessel of interest.

The present description provides preferred exemplary embodiment(s) only, and is not intended to limit the scope, applicability or configuration of the invention. Rather, it is to be understood that various changes may be made in the function and arrangement of elements without departing from the spirit and scope of the invention as set forth in the appended claims.

The invention claimed is:

1. A method for determining emissions in an exhaust plume produced by a combustion engine of a vessel during cruise of the vessel, said emissions comprising the presence or concentration of at least one predetermined gas or the count and size of particles, the method comprising the steps of:

identifying the vessel, its position, bearing and speed;

determining meteorological conditions in an area cruised by the vessel;

providing an unmanned aerial vehicle (UAV) comprising:

an electronic control system for controlling the vehicle's flight;

at least one sensor for determining emissions in the atmosphere surrounding the vehicle;

a data interface of passing signals to an external data collecting unit, said signals comprising at least one of: (a) an output signal of the at least one sensor and (b) data obtained from the output signal of the at least one sensor;

determining a position and distribution of the exhaust plume on the basis of the position, bearing and speed of the vessel and further on the basis of said meteorological conditions;

controlling the UAV to:
fly through the exhaust plume;
determine said emissions in the exhaust plume by means of the at least one in situ sensor for non-optically analyzing gas, air, or the combination thereof; and
transmit said signals to an external data collecting unit for further processing thereof,
wherein the step of controlling the UAV comprises determining or adjusting a flight mission, including at least a flight trajectory for the UAV during flight, and wherein the step of determining or adjusting the flight trajectory is carried out on the basis of meteorological conditions, vessel position, bearing and speed, and sensor data provided by output signals of the at least one sensor in order to navigate the UAV towards a region a highest determinable gas concentration or particle count within the exhaust plume.

2. The method according to claim 1, wherein the meteorological conditions at least include a current, forecasted, or current and forecasted wind speed and wind direction in the area cruised by the vessel.

3. The method according to claim 1, wherein the step of determining said emissions in the exhaust plume comprises the step of sampling sets of data, each set of data comprising sensor data obtained by the at least one sensor, a time of the sample, and a position of the vessel(s) or the UAV at the time of the sample, or the position of the vessel(s) and the UAV at the time of the sample.

4. The method according to claim 1, wherein the UAV comprises an electronic processor for analyzing the sensor data.

5. The method according to claim 1, wherein the emissions determined by the at least one sensor comprise at least carbon dioxide, sulphur dioxide, fine or ultrafine particles, or combinations thereof.

6. The method according to claim 1, wherein the step of controlling the UAV comprises determining a flight mission comprising at least a flight trajectory for the UAV prior to take off, the flight mission optionally including or optionally excluding flight velocities of the UAV.

7. The method according to claim 1, wherein the step of controlling the flight trajectory for the UAV comprises, at least during a part of its flight through the UAV, flying the UAV at a speed and direction which is approximately equal to the vector sum of the speed and direction of the vessel and a current average speed and direction of wind at the vessel's position.

8. The method according to claim 1, wherein the step of controlling the flight trajectory for the UAV comprises, at least during a part of its flight through the UAV, flying the UAV at an approximately constant distance from the vessel, preferably at the center line of the plume.

9. The method according to claim 1, wherein the step of determining or adjusting the flight trajectory is carried out by the control system of the UAV.

10. The method according to claim 9, comprising said step of adjusting the flight trajectory on the basis of at least output signals of the at least one sensor, and wherein adjusting the flight trajectory comprises repeatedly determining a rate of change of a concentration of the emissions, and optionally further the position, course and speed of the vessel(s), and meteorological conditions, and wherein the flight trajectory is adjusted in case said rate of change is negative or otherwise warrants it.

11. The method according to claim 9, wherein the step of adjusting the flight trajectory comprises adjusting a bearing, heading, an altitude of the UAV, or combinations thereof.

12. The method according to claim 1, notably for the determination of sulphur emissions of the vessel, wherein the at least one sensor is arranged within a closed chamber, and wherein:
the flight trajectory of the UAV is controlled or adjusted during its flight, notably on the basis of vessel speed, course, meteorological conditions, sensor data, or combinations thereof;
in situ sensor measurements are carried out by the at least one sensor in said chamber;
and
intake of gas, air, or the combination thereof, into the sensor chamber is controlled for achieving a steady state at the intended measurement site, notably by shutting the air or gas intake at the intended measurement site.

13. An unmanned aerial vehicle (UAV) for determining emissions comprising the presence or concentration of at least one predetermined gas or the count and size of particles, the UAV comprising:
an electronic control system for controlling the vehicle's flight;
at least one sensor for determining emissions in the atmosphere surrounding the vehicle;
a data interface of passing signals to an external data collecting unit, said signals comprising at least one of:
(a) an output signal of the at least one sensor and (b) data obtained from the output signal of the at least one sensor;
the UAV being controllable to:
fly through an area of interest;
determine said emissions in the area of interest by means of the at least one in situ sensor for non-optically analyzing gas, air, or combinations thereof;
transmit said signals to an external data collecting unit for further processing thereof,
wherein the electronic control system is configured to determine or adjust a flight mission, including at least a flight trajectory for the UAV during flight on the basis of meteorological conditions, vessel position, bearing and speed, and sensor data provided by output signals of the at least one sensor in order to navigate the UAV towards a region a highest determinable gas concentration or particle count within the exhaust plume.

14. The unmanned aerial vehicle according to claim 13, wherein the at least one sensor comprises a plurality of sensors arranged in a sealed sensor chamber housed within a fuselage of the UAV, into which air is passed, by sucking by a pump through an air intake provided on an outer surface as well as inside the fuselage of the UAV.

15. The unmanned aerial vehicle according to claim 14 wherein air suction into the sensor chamber is controllable to reach steady state by way of turning on or off the air pump once at least one predetermined concentration threshold is reached.

16. The unmanned aerial vehicle according to claim 13, wherein the at least one sensor comprises a non-optical sensor for chemically or electrochemically analyzing gas, air, or combinations thereof coming into contact with a surface of the sensor.

* * * * *